(12) United States Patent
Spencer et al.

(10) Patent No.: US 11,380,985 B1
(45) Date of Patent: *Jul. 5, 2022

(54) TECHNIQUES FOR PAIN RELIEF

(71) Applicant: nCap Licensing, LLC, Heber City, UT (US)

(72) Inventors: Rhett Francis Spencer, Heber City, UT (US); Anthony Joseph Sutera, Heber City, UT (US)

(73) Assignee: nCap Licensing, LLC, Heber City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/921,814

(22) Filed: Jul. 6, 2020

Related U.S. Application Data

(63) Continuation of application No. 15/920,448, filed on Mar. 13, 2018, now Pat. No. 10,707,570, which is a continuation-in-part of application No. 14/804,018, filed on Jul. 20, 2015, now Pat. No. 9,954,276, which is a continuation of application No. 13/303,135, filed on Nov. 22, 2011, now Pat. No. 9,088,071.

(60) Provisional application No. 62/470,864, filed on Mar. 13, 2017, provisional application No. 61/416,093, filed on Nov. 22, 2010, provisional application No.
(Continued)

(51) Int. Cl.
| | |
|---|---|
| *H01Q 1/24* | (2006.01) |
| *H01Q 1/38* | (2006.01) |
| *H01Q 17/00* | (2006.01) |
| *H01Q 1/52* | (2006.01) |
| *H01Q 1/36* | (2006.01) |

(52) U.S. Cl.
CPC ............... *H01Q 1/526* (2013.01); *H01Q 1/24* (2013.01); *H01Q 1/364* (2013.01); *H01Q 1/38* (2013.01); *H01Q 1/52* (2013.01); *H01Q 17/00* (2013.01); *H01Q 17/004* (2013.01); *Y10T 29/49016* (2015.01)

(58) Field of Classification Search
CPC .......... H01Q 1/526; H01Q 1/24; H01Q 17/00; H01Q 1/38; H01Q 1/52; H01Q 1/364; H01Q 17/004; Y10T 29/49016
USPC .................................................. 343/700 MS
See application file for complete search history.

(56) References Cited

U.S. PATENT DOCUMENTS

| | | | |
|---|---|---|---|
| 6,692,456 B1 * | 2/2004 | Eppstein | A61B 10/0045 600/309 |
| 7,214,847 B1 * | 5/2007 | Flick | A61L 15/18 602/41 |

(Continued)

*Primary Examiner* — Hai V Tran
(74) *Attorney, Agent, or Firm* — Jefferson IP Law, LLP; Raymond B. Persino

(57) ABSTRACT

A method for using a patch for pain relief, and the patch are provided. The method includes determining a location corresponding to source of pain in a body, and disposing a patch including a reactive capacitance material at one of a location corresponding to source of pain or a location between location corresponding to source of pain and a brain. The patch is disposed adjacent to the surface of the body. The reactive the capacitance material comprises conductive particles dispersed in a binder so that at least a majority of the conductive particles are adjacent to, but do not touch, one another. The patch includes a first outer layer, a reactive capacitance layer, and a second outer layer. The reactive capacitance layer is disposed between the first outer layer and the second outer layer. The reactive capacitance layer is formed of the reactive capacitance material.

23 Claims, 7 Drawing Sheets

Related U.S. Application Data

61/473,726, filed on Apr. 8, 2011, provisional application No. 61/477,587, filed on Apr. 20, 2011, provisional application No. 61/514,435, filed on Aug. 2, 2011.

(56) References Cited

U.S. PATENT DOCUMENTS

| | | | |
|---|---|---|---|
| 10,195,148 B2* | 2/2019 | Karpf | A61P 29/00 |
| 2004/0049145 A1* | 3/2004 | Flick | A61F 13/00008 |
| | | | 602/41 |
| 2005/0244484 A1* | 11/2005 | Flick | A61N 1/0468 |
| | | | 424/445 |
| 2007/0239256 A1* | 10/2007 | Weber | A61F 2/82 |
| | | | 623/1.15 |

* cited by examiner

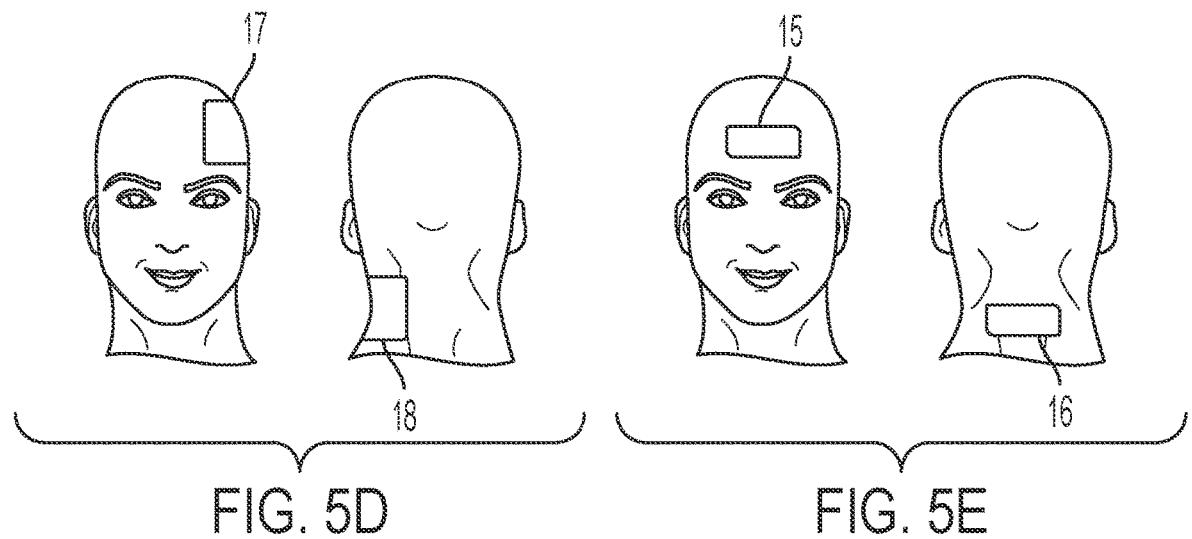
FIG. 5D
FIG. 5E
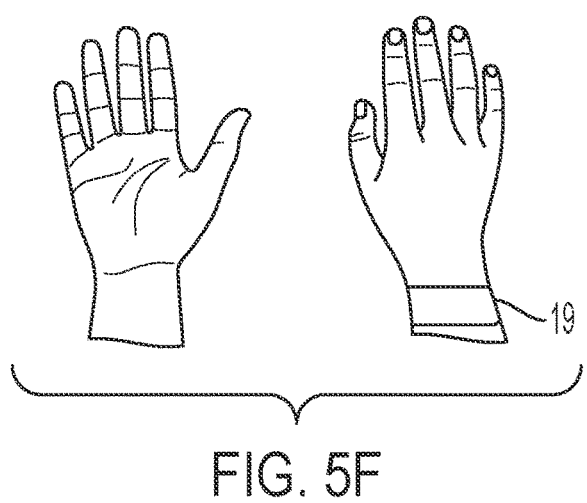
FIG. 5F

TECHNIQUES FOR PAIN RELIEF

CROSS-REFERENCE TO RELATED APPLICATION

This application is a continuation application of prior application Ser. No. 15/920,448, filed on Mar. 13, 2018, which issued as U.S. Pat. No. 10,707,570 on Jul. 7, 2020; which claims the benefit under 35 U.S.C. § 119(e) of a U.S. provisional patent application filed on Mar. 13, 2017 in the U.S. Patent and Trademark Office and assigned Ser. No. 62/470,864, the entire disclosure of which is hereby incorporated by reference. Also, prior application Ser. No. 15/920,448, filed on Mar. 13, 2018, which issued as U.S. Pat. No. 10,707,570 on Jul. 7, 2020, is a continuation-in-part application of prior application Ser. No. 14/804,018, filed on Jul. 20, 2015, which issued as U.S. Pat. No. 9,954,276 on Apr. 24, 2018; which is a continuation application of prior application Ser. No. 13/303,135, filed on Nov. 22, 2011, which issued as U.S. Pat. No. 9,088,071 on Jul. 21, 2015; and which claimed the benefit under 35 U.S.C. § 119(e) of a U.S. provisional patent application filed on Nov. 22, 2010 in the U.S. Patent and Trademark Office and assigned Ser. No. 61/416,093, a U.S. provisional patent application filed on Apr. 8, 2011 in the U.S. Patent and Trademark Office and assigned Ser. No. 61/473,726, a U.S. provisional patent application filed on Apr. 20, 2011 in the U.S. Patent and Trademark Office and assigned Ser. No. 61/477,587, and a U.S. provisional patent application filed on Aug. 2, 2011 in the U.S. Patent and Trademark Office and assigned Ser. No. 61/514,435. The entire disclosure of each of the above identified applications is hereby incorporated by reference in their entirety.

TECHNICAL FIELD

The present disclosure relates to techniques for pain relief.

BACKGROUND

Pain is a normal function of a nervous system. However, the sensation of pain is a discomfort that may be problematic. Thus, there is a need for techniques to relieve pain.

The above information is presented as background information only to assist with an understanding of the present disclosure. No determination has been made, and no assertion is made, as to whether any of the above might be applicable as prior art with regard to the present disclosure.

SUMMARY

An aspect of the present disclosure is to address at least the above-mentioned problems and/or disadvantages and to provide at least the advantages described below. Accordingly, an aspect of the present disclosure is to provide techniques for pain relief.

In accordance with an aspect of the present disclosure, method for using a patch for pain relief is provided. The method includes determining a location corresponding to source of pain in a body, and disposing a patch including a reactive capacitance material at one of a location corresponding to source of pain or a location between location corresponding to source of pain and a brain. The patch is disposed adjacent to the surface of the body. The capacitance material comprises conductive particles dispersed in a binder so that at least a majority of the conductive particles are adjacent to, but do not touch, one another.

In accordance with another aspect of the present disclosure, patch for pain relief is provided. The patch includes a first outer layer, a reactive capacitance layer, and a second outer layer. The reactive capacitance layer is disposed between the first outer layer and the second outer layer. The reactive capacitance layer is formed of a reactive capacitance material comprising conductive particles dispersed in a binder so that at least a majority of the conductive particles are adjacent to, but do not touch, one another.

Other aspects, advantages, and salient features of the present disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of various embodiments of the present disclosure will be more apparent from the following description taken in conjunction with the accompanying drawings, in which:

FIGS. 5A, 5B, 5C, 5D, 5E, and 5F illustrate various locations on a body that a patch including a reactive capacitance material may be disposed according to an exemplary embodiment of the present invention.

Throughout the drawings, like reference numerals will be understood to refer to like parts, components, and structures.

DETAILED DESCRIPTION

Figure 1:
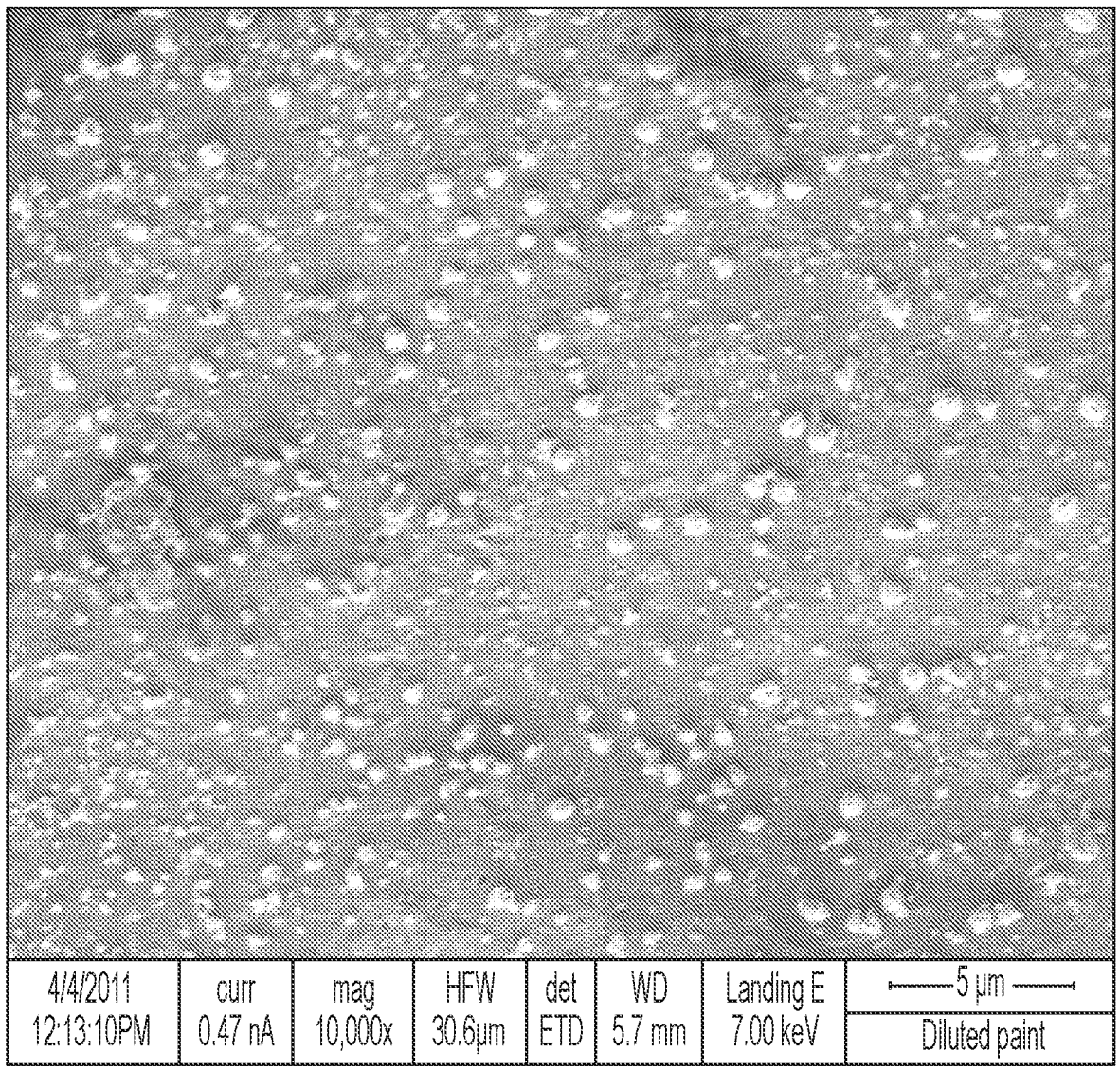
FIG. 1 is a captured image of a reactive capacitance material according to an exemplary embodiment of the present invention.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

As used herein, the term "about" is used to provide flexibility to a numerical range endpoint by providing that a given value may be "a little above" or "a little below" the endpoint.

In addition, various embodiments of the present disclosure described below relate to techniques for pain relief. While the techniques for pain relief may be described below in various specific implementations, the present disclosure is not limited to those specific implementations.

Moreover, while various embodiments of the present disclosure are described herein with respect to a human body, the present disclosure is equally applicable to any animal having a nervous system. Thus, any reference herein to a human nervous system may be substituted is an animal nervous system, such as a cat, dog, horse, pig, bird, cow, etc. Likewise, any reference herein to a part of a human nervous system may be substituted with a corresponding or other part of an animal, such as a cat, dog, horse, pig, bird, cow, etc.

The human nervous system is made up of two main parts, namely the central nervous system and the peripheral nervous system. The central nervous system includes the brain and the spinal cord. The peripheral nervous system includes the sensory and motor nerves.

Sensory nerves send information about what is happening in the peripheral nervous system to the brain via the spinal cord. And the brain sends information back to the motor nerves, which direct motor nerves to perform actions.

Different sensory nerve fibers respond to different things and produce different chemical responses which determine how sensations are interpreted. For example, some nerves send signals associated with light touch, while others respond to deep pressure. Also, special pain receptors called nociceptors activate whenever there has been an injury, or even a potential injury, such as a breaking of the skin or causing a compression of tissue. Once a stimulus is detected by the peripheral nervous system, a nerve impulse is generated and sent through the nerves into the spinal cord, and eventually to the brain.

Those nerve impulses are messages in the form of electrical signals. The electricity of these signals is generated from chemical reactions within nerve cells. Very tiny electrical signals pass from one cell to another through a neural network comprised of dendrites, axons and a synapse gap between the two. Either sodium-gated or calcium-gated ion channels in the plasma membrane generate the electrical action potentials in nerve cells. Thus, while the nervous system utilizes chemical reactions at the cellular level, the nervous system overall may be viewed as an electrical system.

Pain is an intended sensation of the human nervous system. One type of pain is acute pain. With acute pain, when nociceptors detect any tissue damage or potential injury they cause pain sensations. However, after the tissue damage heals or there no longer is a potential injury, the pain sensations stop. This is because the nociceptors no longer detect any tissue damage or potential injury. Thus, acute pain does not persist after the initial injury has healed.

Another type of pain is chronic pain. With chronic pain receptors continue to fire. This is referred to as chronic pain. Chronic pain may be caused by a disease or condition that continuously or repeatedly causes damage. With arthritis, for example, a joint is in a constant state of disrepair, causing pain signals to continuously or repeatedly travel to the brain. Sometimes, even in the absence of tissue damage, nociceptors continue to fire. There may no longer be a physical cause of pain, but the pain response is the same. This makes chronic pain problematic and is often difficult to pin down and even more difficult to treat.

One in three people worldwide suffer from chronic pain, which can greatly interfere with quality of life by impacting mood, limiting activities, and impairing sleep.

There are a number of related-art techniques to relieve pain including techniques that introduce chemicals to the human body, such as herbal remedies and pain medicines (e.g., opioids). Many of these chemically based related-art pain reduction techniques mitigate pain by reducing the effectiveness of the nervous system's ion channels to pass the electric signal, thereby reducing the intensity of the pain signals along with other needed signals to and from the brain. Another example of a related-art technique to relieve pain includes Transcutaneous Electro-Nerve Stimulator (TENS), which is a technique that mitigates pain by injecting an alternative electrical stimulus to distract the brain from registering the pain. Another example of related-art techniques to relieve pain include surgical techniques to either repair or physically block portions of the nervous system.

Many of the related-art pain reduction techniques are limited in effectiveness, have negative side effects, or are otherwise problematic. For example, the related-art pain reduction techniques, such as opioids are dangerous and/or addictive. In addition, many of the related-art pain reduction techniques may prevent the body from healing. This is because many of the related-art pain reduction techniques are designed to interfere with the nervous system either by chemically by interrupting or impairing the communication between the body's pain signals and the brain, by interjecting alternative electrical stimulus to distract the brain from registering the pain, or by physically disrupting the signals in the nervous system.

Accordingly, a technique is needed to mitigate pain that addresses the shortcomings of the related-art pain reduction techniques. In addition, a technique is needed to mitigate pain that is effective. Also, a technique is needed to mitigate pain that is safe. Furthermore, a technique is needed to mitigate pain without hampering healing by the body. In addition, a technique is needed that addresses a compromised nervous system. Still further, a technique is needed that enhances the human nervous system. Moreover, a technique is needed that enhances healing by the body.

Achievement of one or more of the above needs may be possible though a technique that addresses the nervous system as an electrical system. In the context of viewing the nervous system as an electrical system, it is believed that disease or damage to the human body may lead to compromised communication pathways and/or connections in the nervous system. It is further believed that addressing the compromised communication pathways and/or connections in the nervous system, will help mitigate acute pain and/or chronic pain. It is also believed that addressing the compromised communication pathways and/or connections in the nervous system, will help mitigate acute pain and/or chronic pain without hampering healing by the body. It is further believed that facilitating better and/or alternate communication pathways and/or connections in the nervous system may enhance healing by the body. It is still further believed that facilitating better and/or alternate communication pathways and/or connections in the nervous system may addresses a compromised nervous system. It is yet further believed that facilitating better and/or alternate communication pathways and/or connections in the nervous system enhances the human nervous system. It is still further believed that facilitating better and/or alternate communication pathways and/or connections in the nervous system enhances healing by the body. Also, it is believed that facilitating better and/or alternate communication pathways and/or connections in the nervous system is safe.

It has been observed that that a reactive capacitance material disposed in the vicinity of the human body appears to address one or more of the above needs. It has been also observed that that a reactive capacitance material disposed in the vicinity of the human body appears to facilitate better and/or alternate communication pathways and/or connections in the nervous system. It has still further been observed that that a reactive capacitance material disposed in the vicinity of the human body appears to facilitate enhanced sensing of or communication with the nervous system.

It is believed, that disease or damage to the human body may lead to compromised communication pathways and/or connections in the nervous system. It is further believed that addressing the compromised communication pathways and/or connections in the nervous system, will help mitigate acute pain and/or chronic pain without hampering healing by the body. It is further believed that facilitating better and/or alternate communication pathways and/or connections in the nervous system may enhance healing by the body.

An initial overview of the reactive capacitance material is provided below and then specific implementations in which the reactive capacitance material is employed are described in detail further below. This initial overview of the reactive capacitance material is intended to aid readers in understanding the reactive capacitance material that is the basis of various exemplary implementations, but may not identify key features or essential features of those various exemplary implementations, nor is the initial overview of the reactive capacitance material intended to limit the scope of the claimed subject matter.

The reactive capacitance material is unlike any other sensor or electrical coupler used in the medical industry to date. Current medical sensor technology is comprised of inductive coils and skin electrodes. MRI uses very powerful electromagnets and radio frequencies to excite the atoms of the body enough to produce signals strong enough to be detected in the signal coils. ECG and EEG use conductive electrodes connected to high gain amplifiers to measure small electrical signals on the surface of the skin in various places. The signals measured are secondary to the actual signals the brain or heart generates. The signals the brain generates are hundreds of times faster than the ones measured on the skin.

The reactive capacitance material may be capacitive in nature and may be highly sensitive to small electrical signals. One unique feature is its ability to interact with signals of many different frequencies and signal levels simultaneously. By using digital signal processing techniques each unique signal can be separated and analyzed.

These higher fidelity signals will not resemble the signals picked up from the skin sensors, they will contain much more information and once understood will provide advanced diagnostic capabilities.

Detecting these signals without the need to place electrodes and other devices onto the skin will allow for faster testing and eliminate the need for most consumables.

Enhancement of current technology is a possibility but most likely with the filtering of the higher frequency signals will only result in a slight improvement. The reactive capacitance material may be used in passively enhancing the body's natural energy flow. A benefit has been observed when the reactive capacitance material is disposed in the vicinity of the body between an area experiencing pain and the brain.

Reactive Capacitance Material

In one exemplary embodiment, a reactive capacitance material is employed. The reactive capacitance material includes at least two constituent components, namely conductive particles and a binder. However, the reactive capacitance material may include additional components, such as at least one of graphite, carbon (e.g., carbon black), titanium dioxide, etc.

The conductive particles may be any conductive material, such as silver, copper, nickel, aluminum, steel, metal alloys, carbon nanotubes, any other conductive material, and any combination thereof. For example, in one exemplary embodiment, the conductive particles are silver coated copper. Alternatively, the conductive particles may be a combination of a conductive material and a non-conductive material. For example, the conductive particles may be ceramic magnetic microspheres coated with a conductive material such as any of the conductive materials described above. Furthermore, the composition of each of the conductive particles may vary from one another.

The conductive particles may be any shape from a random non-uniform shape to a geometric structure. The conductive particles may all have the same shape or the conductive particles may vary in shape from one another. For example, in one exemplary embodiment, each of the conductive particles may have a random non-uniform shape that varies from conductive particle to conductive particle.

The conductive particles may range in size from a few nanometers up to a few thousand nanometers. Alternatively, the conductive particles may range in size from about 400 nanometers to 30 micrometers. The conductive particles may be substantially similar in size or may be of various sizes included in the above identified ranges. For example, in one exemplary embodiment, the conductive particles are of various sizes in the range of about 400 nanometers to 30 micrometers. Herein, when a range of sizes of the conductive particles are employed, the distribution of the sizes may be uniform or non-uniform across the range. For example, 75% of the conductive particles may be a larger size within a given range while 25% of the conductive particles are a smaller size.

An effective quantity of conductive particles is included relative to the binder so that the conductive particles are dispersed in the binder. The conductive particles may be randomly or orderly dispersed in the binder. The conductive particles may be dispersed at uniform or non-uniform densities. The conductive particles may be dispersed so that at least a majority of the conductive particles are closely adjacent to, but do not touch, one another. When two or more conductive particles touch, they collectively form a single larger particle. At least some of the conductive particles that are adjacent to one another may be capacitively coupled to one another. The reactive capacitance material may have non-ohmic conduction with direct current (DC). The density of the conductive particles may be below the percolation limit for DC electrical conduction. AT DC, the conductive particles density may be below the percolation path or percolation backbone. The DC response may be different than the RF response. The conductive particles may not provide an end to end DC conductive path since the majority of the conductive particles may be isolated from each other and do not touch. Unlike conductive inks that when cured create conductive paths, the conductive particles when cured in the binder may not create or contain such conductive paths.

The binder is used to substantially fix the conductive particles relative to each other and should be a non-conductive or semi-conductive substance. Any type of conventional or novel binder that meets these criteria may be used. The non-conductive or semi-conductive material of the binder may be chosen to function as a dielectric with a given permittivity.

The reactive capacitance material may be formed as a rigid or semi-rigid structure. For example, the reactive capacitance material may be a plastic sheet having the conductive particles dispersed therein. The reactive capacitance material may be clear or opaque, and may include any shade of color.

In addition, the reactive capacitance material may be a liquid, paint, gel, ink or paste that dries or cures. Here, the binder may include distillates, hardening agents, or solvents such as a Volatile Organic Compound (VOC). In this case, the reactive capacitance material may be applied to a substrate. The reactive capacitance material may be applied to less than all of the substrate or to all of the substrate. Also, the reactive capacitance material may extend off the substrate if the reactive capacitance material is applied to less than all of the substrate or to all of the substrate. Also, when the reactive capacitance material is a liquid, paint, gel, ink or paste that dries or cures, the binder may adhere to the substrate. The reactive capacitance material may be sprayed on, brushed on, rolled on, ink-jet printed, silk screened, etc. onto the substrate. The use of the reactive capacitance material that is a liquid, paint, gel, ink or paste that dries or cures is advantageous in that the reactive capacitance material may be thinly applied to a substrate and conform to the surface of the substrate. This allows the reactive capacitance material to occupy very little space and, in effect, blend into the substrate.

The substrate may be the surface of one or more of conductive, non-conductive, semi-conductive substance, or any combination thereof. The substrate may be the human body or a human body interface of a sensor. The substrate may be rigid, semi-flexible or flexible. The substrate may be flat, irregularly shaped or geometrically shaped. The substrate may be one or more of paper, cloth, plastic, polycarbonate, acrylic, nylon, polyester, rubber, metal such as aluminum, steel and metal alloys, glass, composite materials, fiber reinforced plastics such as fiberglass, polyethylene, polypropylene, fiberglass, textiles, wood, or any combination thereof.

The substrate may have a coating applied thereto. The coating may be at least one of a conductive, non-conductive, or semi-conductive substance. The coating may be a paint, gel, ink, paste, tape, etc. The coating may be chosen to function as a dielectric with a given permittivity.

At least one of a protective and concealing (or decorative) coating may be applied over the reactive capacitance material once it has been applied to a substrate. The at least one of a protective and concealing (or decorative) coatings applied over the reactive capacitance material may be smaller than the substrate or area of the substrate including the reactive capacitance material, the same size as the substrate or area of the substrate including the reactive capacitance material, or larger than the substrate or area of the substrate including the reactive capacitance material.

Similarly, at least one of a protective and concealing (or decorative) coating may be applied under the substrate. The at least one of a protective and concealing (or decorative) coatings applied under the substrate may be smaller than the substrate, the same size as the substrate, or larger than the substrate.

An example of the reactive capacitance material is described below with reference to FIG. 1.

FIG. 1 is a captured image of a reactive capacitance material according to an exemplary embodiment of the present invention.

Referring to FIG. 1, the reactive capacitance material includes conductive particles and a binder. The conductive particles are randomly shaped, sized and located. However, conductive particles are dispersed so that at least a majority of the conductive particles are closely adjacent to, but do not touch, one another.

Herein, without intending to be limiting, for a reactive capacitance material of a given density of conductive particles, the reactive capacitance material may be applied at a thickness such that the conductive particles are dispersed in the binder so that at least a majority of the conductive particles are closely adjacent to, but do not touch, one another. Herein, without intending to be limiting, it has been observed that a reactive capacitance material may be applied to have a resistance of about 3-17 ohms across any given two points on the surface.

Herein, without intending to be limiting, it has been observed that when the reactive capacitance material is formulated such that the conductive particles are dispersed in the binder so that at least a majority of the conductive particles are closely adjacent to, but do not touch, one another, the reactive capacitance material exhibits properties that enable it to at least one of efficiently propagate electromagnetic radiation and/or bioelectromagnetic radiation, efficiently absorb electromagnetic radiation and/or bioelectromagnetic radiation, and efficiently emit electromagnetic radiation and/or bioelectromagnetic radiation. Moreover, it has been observed that those properties may be either supplemented or enhanced by including an effective amount of carbon, such as carbon black, in the reactive capacitance material. For example, an effective amount of carbon black may be an amount that corresponds to about 1-7% of the conductive particles included in the reactive capacitance material.

Without intending to be limiting, it is believed that when electromagnetic radiation is introduced into the reactive capacitance material, electromagnetic radiation and/or bioelectromagnetic radiation may pass from conductive particle to conductive particle via at least one of capacitive or inductive coupling. Here, the binder may function as a dielectric. Thus, it is believed that the reactive capacitance material may act as an array of capacitors, which may be at least part of the reason why the reactive capacitance material at least one of efficiently propagates electromagnetic radiation and/or bioelectromagnetic radiation, efficiently absorbs electromagnetic radiation and/or bioelectromagnetic radiation, and efficiently emits electromagnetic radiation and/or bioelectromagnetic radiation.

Alternatively or additionally, and without intending to be limiting, it is believed that the properties that enable the reactive capacitance material to at least one of efficiently propagate electromagnetic radiation and/or bioelectromagnetic radiation, efficiently absorb electromagnetic radiation and/or bioelectromagnetic radiation, and efficiently emit electromagnetic radiation and/or bioelectromagnetic radiation, may be explained by quantum theory at the atomic level.

Herein, without intending to be limiting, it has been observed that the reactive capacitance material generates electrical energy when exposed to sunlight.

Herein, without intending to be limiting, it has been observed that the resistance of the reactive capacitance material continuously changes over time. Herein, without intending to be limiting, it has been observed that, when energized with a radio signal, the reactive capacitance material has infinitely low resistance to that signal.

Use of Reactive Capacitance Material with Nervous System

As indicated above, a benefit has been observed when the reactive capacitance material is disposed in the vicinity of the body between an area experiencing pain and the brain. It is believed that the reactive capacitance material enhances the communication of body's nerve impulses. The reactive capacitance material may enhance the communication of body's nerve impulses in at least one of nerve impulses communicated the direction towards the brain, nerve impulses communicated the direction away from the brain, or bi-directionally. The reactive capacitance material may enhance the communication of body's nerve impulses at least one of between the central nervous system and the peripheral nervous system, within the central nervous system, within the peripheral nervous system, between the brain and the outer nerves, or among a local grouping of nerves.

By enhancing the communication of body's nerve impulses, the brain may more clearly receive the pain signals, which may better enable the brain to assist in the body's natural healing processes. For example, instead of mitigating the communication of pain signals to the brain, instead of distracting, confusing or overstimulating the brain, and instead of blocking the pain signals, the reactive capacitance material may assist in enabling better reception by the brain of the pain signal, and thereby may place the brain in a better position to resolve the pain.

By using the reactive capacitance material to enhance the communication of body's nerve impulses, the brain may better and/or more quickly identify and resolve pain. By lowering pain, a feeling of well-being is re-established. It has been observed that the reactive capacitance reduces pain and shortens the direction pain is experienced.

The use of the reactive capacitance material to relieve pain may be beneficial in at least one of its effectiveness, reduction in duration of pain, safe use, or lack of side effects. Also, when using the reactive capacitance material to relieve pain, the reactive capacitance material is not consumed and thus may be reused. In addition, use of the reactive capacitance material to relieve pain may be non-invasive.

Examples of pain that the reactive capacitance material may treat includes at least one of neuropathy, restless leg syndrome, fibromyalgia, back pain, knee pain, arthritis, shoulder pain, headaches, swelling, stiffness, tooth aches, foot pain, or any other pain the body might experience.

It is noted that the reactive capacitance material may not eliminate the cause of the pain and may not be a cure. However, by using the reactive capacitance material to enhance the communication of body's nerve impulses, the body may at least one of target the source of pain, better perform the natural healing process, reduce the user's focus on pain, or provide relief from pain.

Patch Employing Reactive Capacitance Material

The reactive capacitance material may be implemented as a patch.

Figure 2:
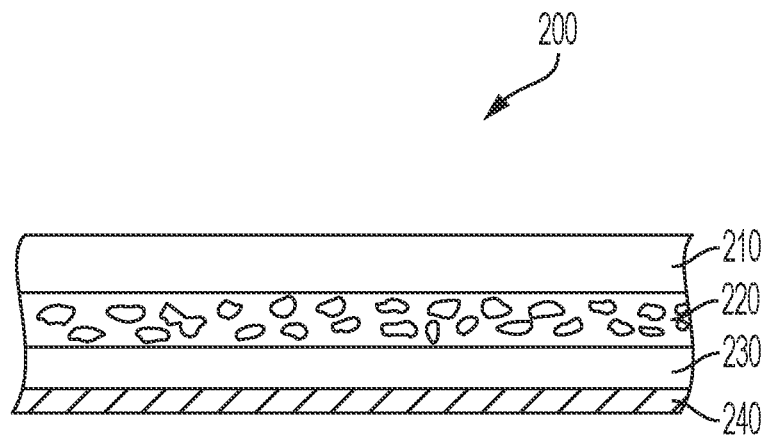
FIG. 2 illustrates a structure the reactive capacitance material implemented as a patch according to an exemplary embodiment of the present invention.

FIG. 2 illustrates a structure the reactive capacitance material implemented as a patch according to an exemplary embodiment of the present invention.

Referring to FIG. 2, a patch 200 includes a plurality of layers including a first outer layer 210, reactive capacitance material 220, substrate 230, and a second outer layer 240.

The reactive capacitance material 220 and substrate 230 are described above, and thus a description thereof will be omitted for conciseness. First outer layer 210 and second outer layer 240 serve to protect the reactive capacitance material 220 and substrate 230. First outer layer 210 and second outer layer 240 may be the same material or different materials. First outer layer 210 and second outer layer 240 may be a non-allergenic material. The substrate 230 may be omitted. When the substrate 230 is omitted, one of the first outer layer 210 and the second outer layer 240 additionally functions as the substrate 230. Also, additional layers may be included in patch 200. The patch 200 is flexible enough to conform to the body. The patch 200 may include an adhesive or other fastening structure. The first outer layer 210 and the second outer layer 240 may encase the reactive capacitance material 220 and substrate 230.

Figure 3:
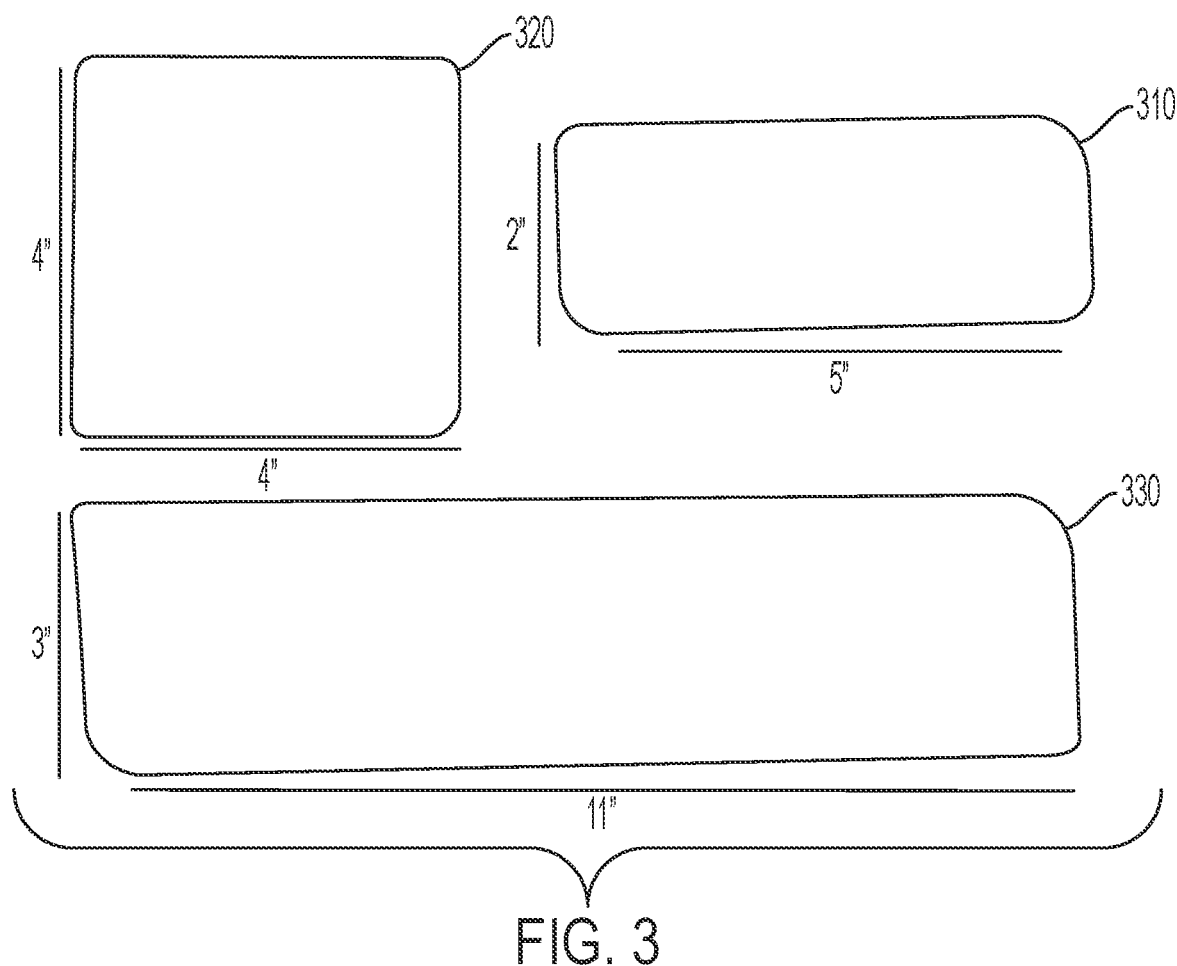
FIG. 3 illustrates various structures of a patch including a reactive capacitance material according to an exemplary embodiment of the present invention.

FIG. 3 illustrates various structures of a patch including a reactive capacitance material according to an exemplary embodiment of the present invention.

Referring to FIG. 3, patch 310, patch 320, and patch 330 are shown in various sizes. Patch 310 is substantially 2×5 inches, which may be an appropriate size for use for necks, headaches and limbs. Patch 320 is substantially 4×4 inches, which may be an appropriate size for use for shoulders, menstrual pain, legs or knees. Patch 330 is substantially 3×11 inches, which may be an appropriate size for use for backs, legs or stomach pains, and may be easy to sleep on.

Figure 4:
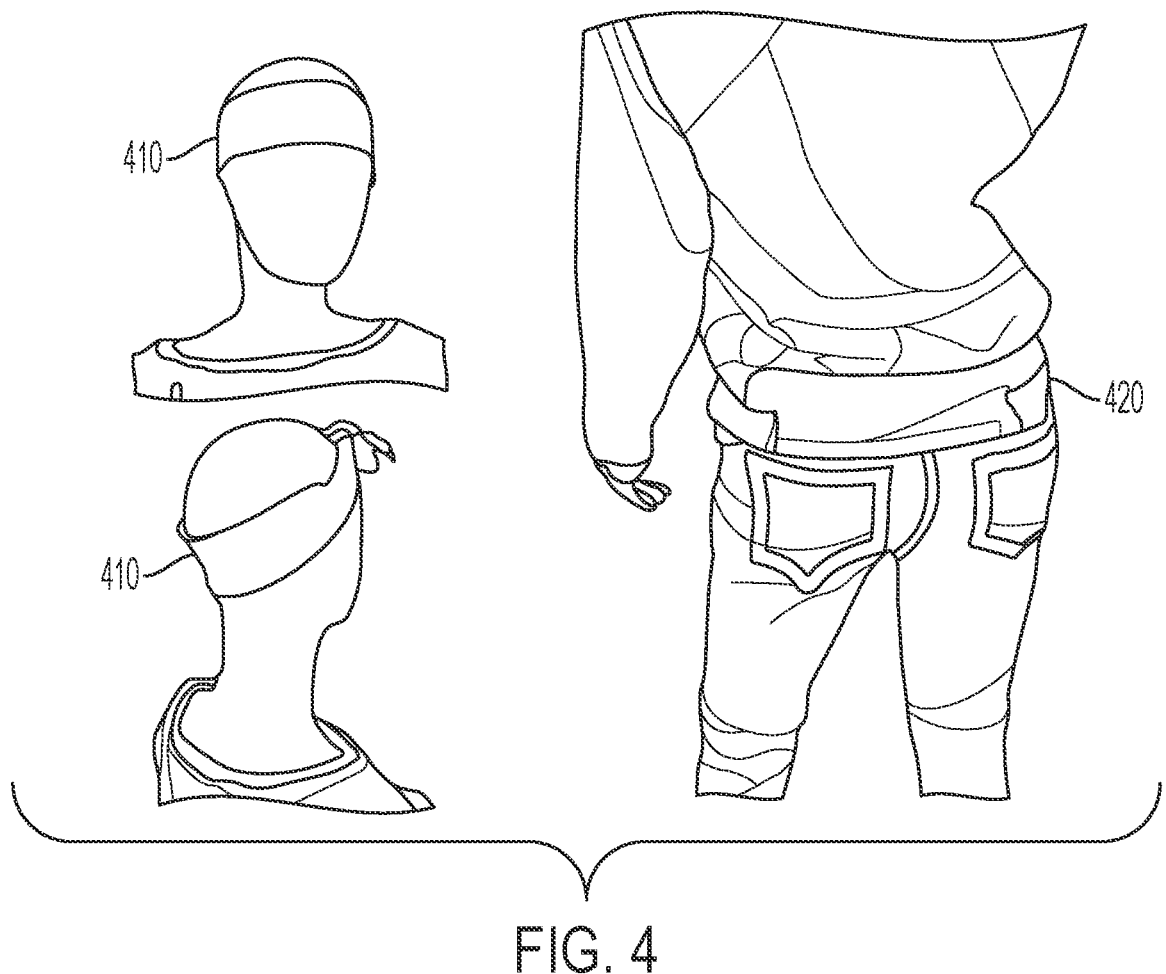
FIG. 4 illustrates various structures of holder for a patch including a reactive capacitance material according to an exemplary embodiment of the present invention.
Figure 5A:
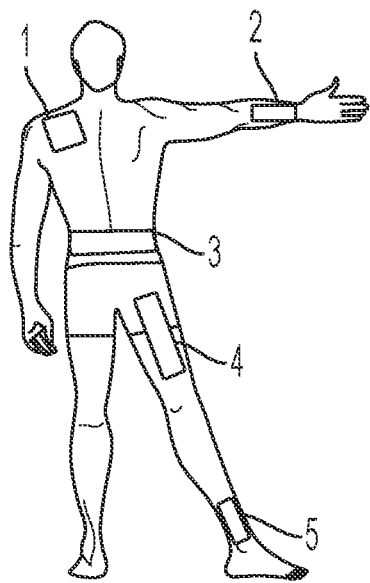
Figure 5B:
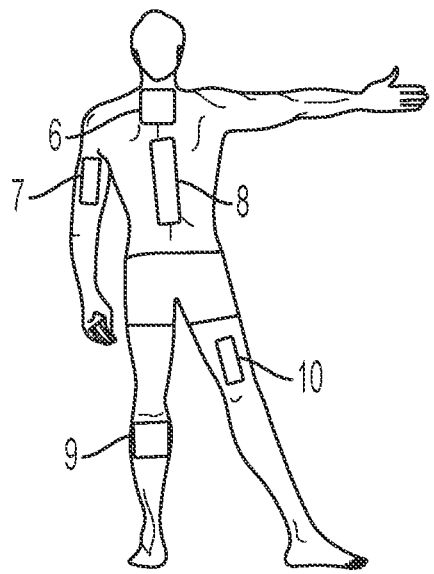
Figure 5C:
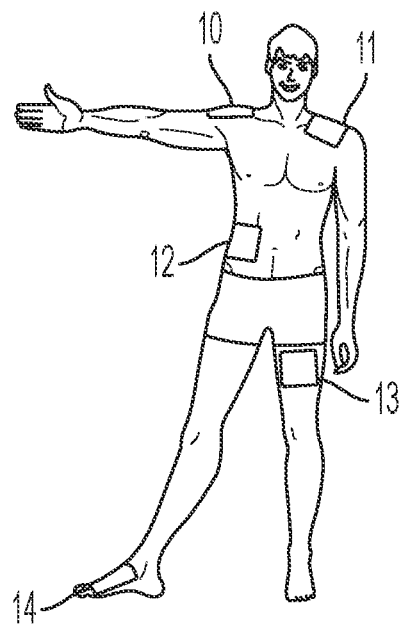

FIG. 4 illustrates various structures of holder for a patch including a reactive capacitance material according to an exemplary embodiment of the present invention.

The patch including the reactive capacitance material may be used in conjunction with a holder. Referring to FIG. 4, the patch may be used with a wrap 410 that holds the patch, such as patch 310, that may, for example, be used with the head, neck or limbs. When the pain relief device is used with wrap 410, the wrap 410 wraps around the body to retain the patch against the body. Also, the patch may be used with an adjustable belt and pocket combination 420 that holds the patch, such as patch 320 or patch 330, that may, for example, be used around the torso. When the pain relief device is used with the adjustable belt and pocket combination 420, the adjustable belt and pocket combination 420 wraps around the body to retain the patch against the body.

FIGS. 5A, 5B, 5C, 5D, 5E, and 5F illustrate various locations on a body that a patch including a reactive capacitance material may be disposed according to an exemplary embodiment of the present invention.

Referring to FIGS. 5A, 5B, 5C, 5D, 5E, and 5F, a patch including a reactive capacitance material may be disposed in various locations of the body to treat various sources of pain. Locations and/or sources of pain include: shoulder and arm 1; hand 2; sciatica and leg 3; knee and leg 4; foot and ankle 5; upper back 6; elbow, arm, hand 7; lower back 8; lower leg, ankle, foot 9; knee, lower leg, foot 10; shoulder, rotator 10, shoulder 11; cramps, bowel 12; upper leg, knee 13; foot, toes, gout 14; migraine, headache 15; neck, tension headache 16, headache, trigeminal neuralgia 17; neck, tension headache 18; and hand, arthritis 19.

Figure 6:
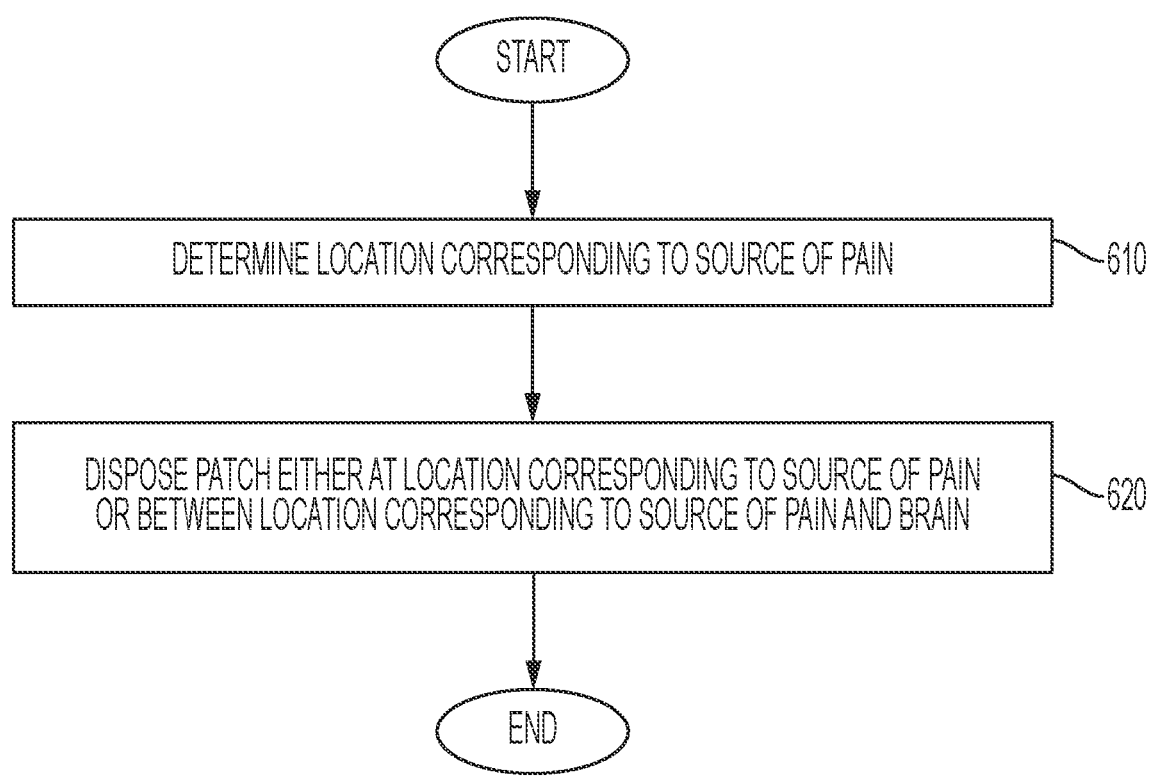
FIG. 6 illustrates a method for using a patch including a reactive capacitance material according to an exemplary embodiment of the present invention.

FIG. 6 illustrates a method for using a patch including a reactive capacitance material according to an exemplary embodiment of the present invention.

Referring to FIG. 6, a location corresponding to source of pain is determined in step 610. In step 620, a patch including a reactive capacitance material is disposed either at location corresponding to source of pain or between location corresponding to source of pain and brain.

The patch including the reactive capacitance material may be implemented as a plurality of different devices and method of use thereof. Examples of various implementations are provided below.

In one exemplary implementation, the patch including the reactive capacitance material may be implemented as a pain relief device and method of use thereof.

A pain relief device and method of application for topical application to a body to provide symptomatic pain relief is described herein. The pain relief may be from any of one or more conditions such as at least one of arthritis, broken bones, cancer, phantom limb pain, or other conditions causing pain. The device can be applied or worn directly to the skin or in closely fitting clothing to keep it in near proximity to the body. The location of the device is semi dependent on the area requiring relief, such as surrounding an injured area for the treatment, reduction of joint inflammation, edema and excitation of neural stimulation associated with human and mammal tissues.

The pain relief device may include an outer layer. The outer layer may be a non-allergenic material. Also, the pain relief device may include one or more inner layers. In addition, the pain relief device may include one or more reactive capacitance layers.

The pain relief device may be affixable to a portion of a body or clothing. Also, the pain relief device may be placed in a garment pocket. In addition, the pain relief device can be worn draped around the neck and hang loosely down the front of the body. The pain relief device may be secured with elastic wrap. Further, pain relief device may be secured with tape. Also, pain relief device can be held in place using hook and loop fasteners. In addition, the pain relief device may be sewn into a garment. Moreover, the pain relief device may be loosely wrapped around a body or limb. Also, the pain relief device may be held in place using safety pins or any other commercially available fasteners, tapes or wraps.

In another implementation, the reactive capacitance material may be implemented as a passive device for correcting color blindness and method of use thereof.

The passive device for correcting color blindness may include an outer layer. The outer layer may be a non-allergenic material. Also, the passive device for correcting color blindness may include one or more inner layers. In addition, the passive device for correcting color blindness may include one or more reactive capacitance layers.

The passive device for correcting color blindness may be affixable to a head or clothing, and may, for example, be held in place with a baseball or other form of a cap. Also, the passive device for correcting color blindness may be placed in a garment pocket. The passive device for correcting color blindness may be secured with elastic wrap. Further, passive device for correcting color blindness may be secured with tape. Also, the passive device for correcting color blindness may be held in place using safety pins or any other commercially available fasteners, tapes or wraps.

In yet another implementation, the reactive capacitance material may be implemented as a passive neural stimulation device for treatment of chronic inflammation and method of use thereof. The passive system for treating chronic inflammation enhances the body's natural energy and immune system.

The passive device for treatment of chronic inflammation may include an outer layer. The outer layer may be a non-allergenic material. Also, the passive device for treatment of chronic inflammation may include one or more inner layers. In addition, the passive device for treatment of chronic inflammation may include one or more reactive capacitance layers.

The passive device for treatment of chronic inflammation may be affixable to a body or clothing. Also, the passive device for treatment of chronic inflammation may be placed in a garment pocket. In addition, the passive device for treatment of chronic inflammation may be worn draped around the neck and hang loosely down the front of the body. The passive device for treatment of chronic inflammation may be secured with elastic wrap. Further, passive device for treatment of chronic inflammation may be secured with tape. Moreover, the passive device for treatment of chronic inflammation may be held in place using hook and loop fasteners. In addition, the passive device for treatment of chronic inflammation may be sewn into a garment. Also, the passive device for treatment of chronic inflammation may be held in place using safety pins or any other commercially available fasteners, tapes or wraps.

In still another implementation, the reactive capacitance material may be implemented as a medical device for effecting faster healing of orthopedic and other wounds, and method of use thereof. The medical device and method may be used at a wound to facilitate the rapid healing of the tissue at the situs of the wound with minimal fibrous tissue formation. The medical device is arranged to be brought into close proximity or adjacent to the wound.

The medical device may include an outer layer. The outer layer may be a non-allergenic material. Also, the medical device may include one or more inner layers. In addition, the medical device may include one or more reactive capacitance layers.

The medical device may be affixable near to, over or adjacent a wound. Also, the medical device may be secured with elastic wrap. In addition, the medical device may be secured with tape. Moreover, the medical device may be held in place using hook and loop fasteners. Furthermore, the medical device may be held in place using hook and loop fasteners. In addition, the medical device may be sewn into a garment. Also, the medical device may be held in place using safety pins or any other commercially available fasteners, tapes or wraps.

Other Uses of the Reactive Capacitance Material

The reactive capacitance material may be implemented in other than the patch. For example, instead of the reactive capacitance material being applied to a substrate, the reactive capacitance material may be directly applied onto the skin of a body. Here, a protective layer may be applied over the reactive capacitance material applied to the skin.

In yet another example, the reactive capacitance material may be utilized within a structure configured to be inserted into the body either temporality or permanently.

In still another example, the reactive capacitance material may be placed on sensors used to detect bioelectromagnetic radiation and/or electrical signals from a biological source. Here, the reactive capacitance material facilitates better communication of the electrical energy, electromagnetic radiation and/or bioelectromagnetic radiation. The reactive capacitance material may be disposed directly onto at least one of a conductive portion or a non-conductive portion of the sensor. In addition, the reactive capacitance material may be disposed adjacent to the sensor.

In yet another example, the reactive capacitance material may be used to facilitate a better transmission of electrical energy into the human body. For example, the reactive capacitance material may be used with the leads of a TENS device, with the paddles of a defibrillator, with ultrasound and sonogram machine, etc.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A method for using a patch for pain relief for a body comprising a nervous system, the method comprising:
   disposing the patch adjacent to a surface of the body at one of a first location on the body corresponding to a source of pain in the body or a second location on the body between the first location and a brain of the body, wherein the patch includes:
      a first non-conductive outer layer,
      a reactive capacitance layer, and
      a second non-conductive outer layer,
   wherein the reactive capacitance layer is disposed between the first non-conductive outer layer and the second non-conductive outer layer so as to encase and electrically isolate the reactive capacitance layer, and
   wherein the reactive capacitance layer is formed of a reactive capacitance material comprising conductive particles dispersed in a binder so that at least a majority of the conductive particles are adjacent to, but do not touch, one another.

2. The method of claim 1, wherein the body is a human body.

3. The method of claim 1, wherein the body is non-human body.

4. The method of claim 1, wherein the reactive capacitance layer conforms to at least one of a surface of the first non-conductive outer layer or a surface of the second non-conductive outer layer.

5. The method of claim 1, wherein the patch is flexible so as to conform to the surface of the body at the one of the first location on the body or the second location on the body.

6. The method of claim 1, wherein the reactive capacitance layer has a resistance of 3-17 ohms across any two points thereof.

7. The method of claim 1, wherein at least one of the first non-conductive outer layer or the second non-conductive outer layer is formed from a non-allergenic material.

8. The method of claim 1, wherein the patch includes one or more additional reactive capacitance layers.

9. The method of claim 1, wherein the patch further includes one or more layers between the first non-conductive outer layer and the second non-conductive outer layer in addition to the reactive capacitance layer.

10. The method of claim 1, wherein the surface of the body is inside the body.

11. The method of claim 1, wherein the patch further includes at least one of an adhesive or fastening structure to fix the patch adjacent to the surface of the body.

12. The method of claim 1, wherein, when the patch is disposed adjacent to the surface of the body, the reactive capacitance layer couples to the nervous system of the body.

13. A patch for pain relief for a body comprising a nervous system, the patch comprising:
   a first non-conductive outer layer;
   a reactive capacitance layer; and
   a second non-conductive outer layer,
   wherein the reactive capacitance layer is disposed between the first non-conductive outer layer and the second non-conductive outer layer so as to encase and electrically isolate the reactive capacitance layer, and
   wherein the reactive capacitance layer is formed of a reactive capacitance material comprising conductive particles dispersed in a binder so that at least a majority of the conductive particles are adjacent to, but do not touch, one another.

14. The patch of claim 13, wherein the body is a human body.

15. The patch of claim 13, wherein the body is non-human body.

16. The patch of claim 13, wherein the reactive capacitance layer conforms to at least one of a surface of the first non-conductive outer layer or a surface of the second non-conductive outer layer.

17. The patch of claim 13, wherein the patch is flexible so as to conform to a surface of the body.

18. The patch of claim 13, wherein the reactive capacitance layer has a resistance of 3-17 ohms across any two points thereof.

19. The patch of claim 13, wherein at least one of the first non-conductive outer layer or the second non-conductive outer layer is formed from a non-allergenic material.

20. The patch of claim 13, wherein the patch includes one or more additional reactive capacitance layers.

21. The patch of claim 13, wherein the patch further includes one or more layers between the first non-conductive outer layer and the second non-conductive outer layer in addition to the reactive capacitance layer.

22. The patch of claim 13, wherein the patch further includes at least one of an adhesive or fastening structure to fix the patch adjacent to a surface of the body.

23. The patch of claim 13, wherein, when the patch is disposed adjacent to a surface of the body, the reactive capacitance layer couples to the nervous system of the body.

* * * * *